United States Patent [19]
Van Egmond et al.

[11] Patent Number: 5,709,661
[45] Date of Patent: Jan. 20, 1998

[54] ELECTRONIC CATHETER DISPLACEMENT SENSOR

[75] Inventors: Franciscus Cornelis Van Egmond, Heenvliet; Charles Theodoor Lancee, Waarder, both of Netherlands

[73] Assignee: Endo Sonics Europe B.V., Eijswijk, Netherlands

[21] Appl. No.: 325,196

[22] PCT Filed: Apr. 14, 1992

[86] PCT No.: PCT/NL92/00072

§ 371 Date: Dec. 22, 1994

§ 102(e) Date: Dec. 22, 1994

[87] PCT Pub. No.: WO93/20876

PCT Pub. Date: Oct. 28, 1993

[51] Int. Cl.[6] .................................................. A61M 5/00
[52] U.S. Cl. ........................... 604/117; 604/174; 33/512
[58] Field of Search ............................... 33/512; 604/117, 604/116, 174, 178, 179

[56] References Cited

U.S. PATENT DOCUMENTS

| 4,644,157 | 2/1987 | Ozawa | 250/231 |
| 5,297,346 | 3/1994 | Weiner | 33/512 |

*Primary Examiner*—Sam Rimell
*Assistant Examiner*—Luke Yeh
*Attorney, Agent, or Firm*—Thomas R. Vigil

[57] ABSTRACT

The electronic catheter displacement sensor comprises a displacement sensing roller and an idler roller between which a catheter can be advanced or retracted, circuitry for sensing the rotation of the displacement sensing roller, circuitry for determining the direction in which the displacement sensing roller is rotated, and circuitry coupled to said rotation sensing circuitry and to said direction sensing circuitry for generating an output signal for transmission to a visual display device for displaying the distance the catheter has been advanced or retracted. The rollers can be mounted in a sensor unit separable from the displacement sensor and the sensor unit is preferably disposable.

7 Claims, 7 Drawing Sheets

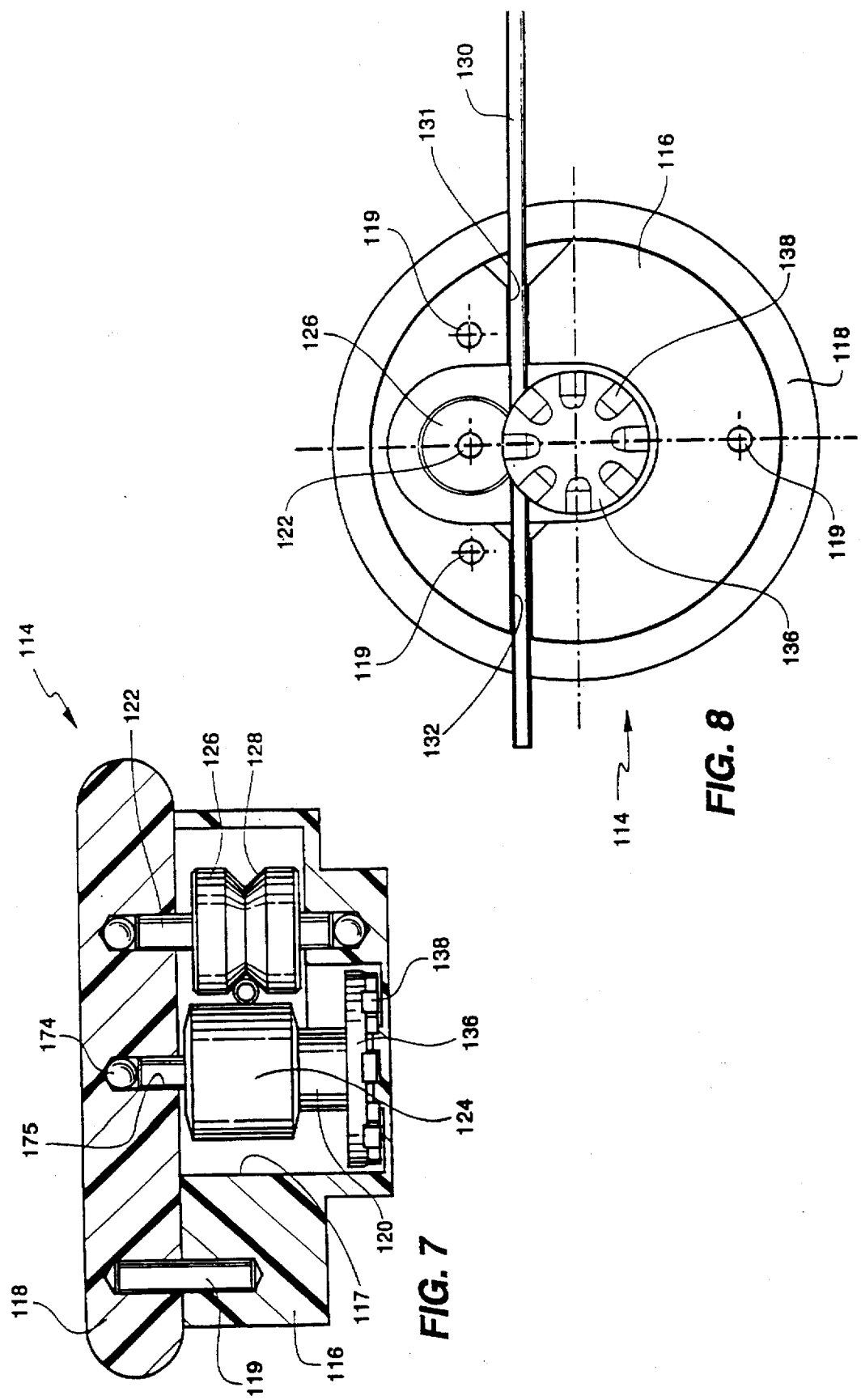

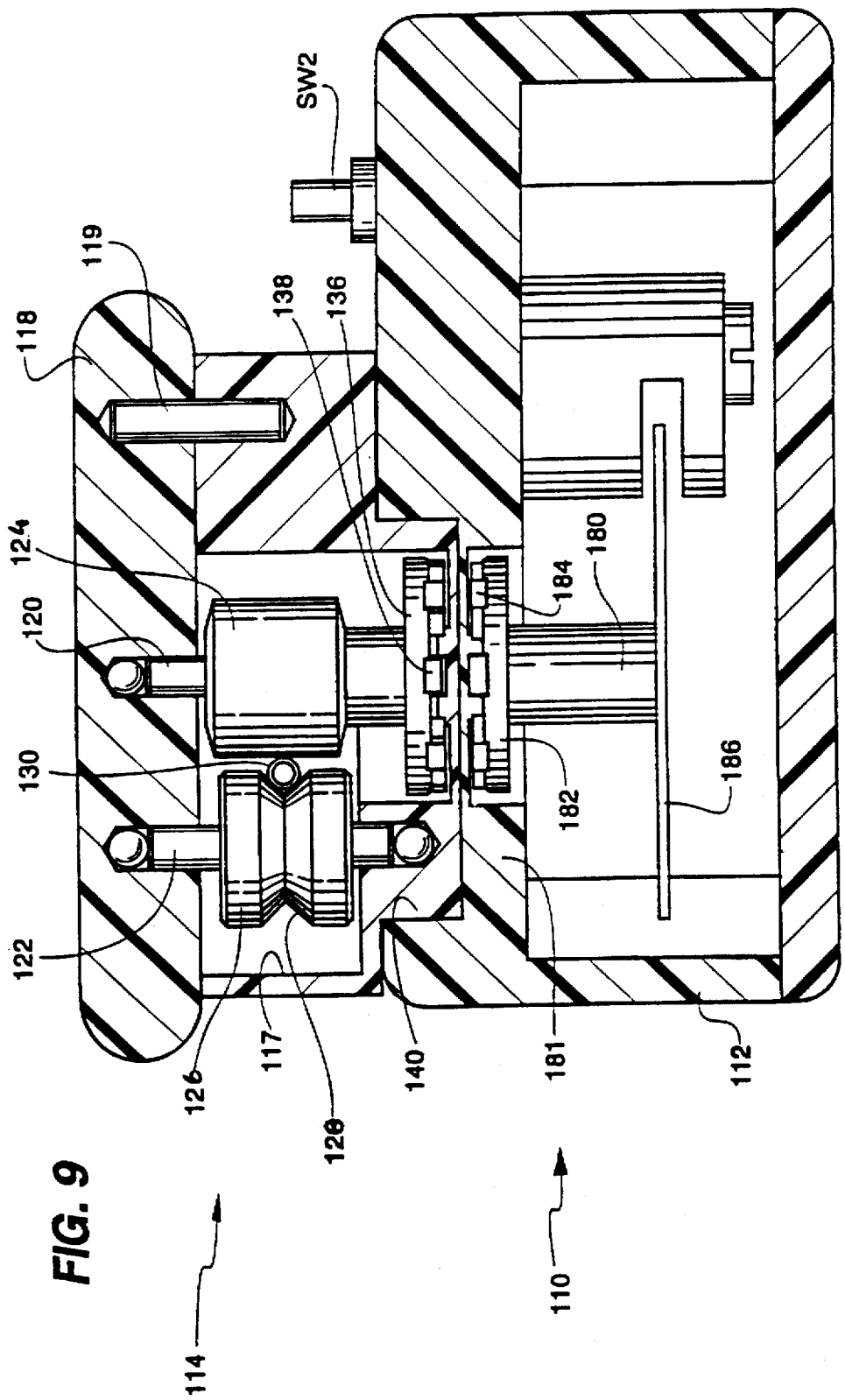

ELECTRONIC CATHETER DISPLACEMENT SENSOR

BACKGROUND OF THE INVENTION

1. Field of the Invention

The present invention relates to an electronic catheter displacement sensor which senses the advancement of a catheter as the catheter is pushed or pulled through the sensor. The sensor generates signals which are supplied to electronic processing circuitry that converts the signals to signals indicative of a unit of distance and indicative of direction of movement of the catheter and these distance signals can then be supplied to a visual display device such as a video screen. The distance which the catheter has been advanced, such as during advancement of the catheter into a blood vessel in a body, then can be displayed on the video screen.

The invention is also directed to a disposable sensor unit of the displacement sensor through which the catheter is advanced and/or retracted so that each time the displacement sensor is used with a new catheter, a new sterile sensor unit can be mounted in the displacement sensor thereby to prevent contamination of the new catheter.

2. Description of Prior Art

Heretofore various devices have been proposed for advancing catheters into body cavities or blood vessels. Examples of such prior art devices are disclosed in the following patent publications:

| U.S. Pat. No. | Patentee |
| --- | --- |
| 3,835,854 | Jewett |
| 4,401,433 | Luther |
| 4,563,176 | Gustavsson et al. |
| 4,616,648 | Simpson |
| 4,846,171 | Kauphusman et al. |
| 4,917,094 | Lynch et al |
| Published European Patent Specification No. 0 050 606 | Gustavvson et al. |

The Jewett U.S. Pat. No. 3,835,854 discloses a device for advancing a catheter between two nip rollers, one being an idler roller and one being a drive roller. A knob is connected to the drive roller whereby rotation of the knob will advance the catheter into a needle upon rotation of the knob. The Luther U.S. Pat. No. 4,401,433 discloses an apparatus for advancing an oversized catheter through a cannula by folding the catheter and then passing the folded catheter through advancing roller drives which are rotated to advance the catheter through a cannula and thence into a patient.

The Gustavvsson et al. U.S. Pat. No. 4,563,176 discloses a device for sterile storage of a catheter and the sterile advancing thereof. A ratchet mechanism or a movable handle are provided for advancing the catheter. The catheter is received through a sterile transparent plastic sheath having a movable scale thereon, the zero point of the scale being aligned with a coupling piece at the proximal end of the catheter. As the catheter is advanced out of the protective sheath, the position of the coupling piece relative to the scale indicates how far into the body the catheter has been advanced.

The Simpson U.S. Pat. No. 4,616,648 discloses a device for facilitating the exchange of dilatation catheters during an angioplasty procedure. The device includes first and second friction rollers and a rotatable member for causing rotation of friction rollers to move an exchange guidewire into tubing mounted within a housing coupled to a guiding catheter for inserting an exchange guidewire into the guiding catheter.

The Kauphusman et al. U.S. Pat. No. 4,846,171 discloses a laser catheter adjustable control apparatus including an optic fiber advance housing having a fiber advance assembly mounted therein for reciprocal movement. The advancing mechanism has ratchet teeth such that the ratchet teeth on a movable part will engage the optic fiber for moving same when the movable part is depressed and moved longitudinally by a physician.

The Lynch et al U.S. Pat. No. 4,917,094 discloses a guidewire advancement system including a housing through which a guidewire extends, an opening in the housing and a slide bar mounted in the opening. The slide bar can be depressed against the guidewire and then moved axially with the guidewire toward a patient to move the guidewire incrementally into an artery of the patient. A monitor can be electrically connected to the slide bar for establishing an electrical connection through the guidewire (when the slide bar touches the guidewire) to the tip of the guidewire to pick up electrical heart pulses as the guidewire tip approaches the heart.

European Patent Publication No. 0 050 606 discloses a disk shaped dispensing container mounting a venous catheter therein. The venous catheter exits the container between two rollers, one being an idler roller and the other being a drive roller. A shaft extends from the drive roller outside the container to a knob. Mounted within the container, on the shaft and adjacent a window in the container is a gear wheel which acts upon a gear ring. A flange of the gear ring has scale graduations thereon which are exposed through the window. In this way, rotation of the knob to advance the venous catheter will rotate the gear ring to indicate by the scale graduation appearing in the window how far the catheter has been advanced from the container.

As will be described in greater detail hereinafter, the catheter displacement sensor differs from the prior advancing system described above by being electronic including an electrical-magnetic sensor, by providing digital output signals for viewing on a television screen of the distance a catheter has been inserted or withdrawn and by providing a disposable sensor which is isolated in a sterile manner from the electronics of the displacement sensor.

SUMMARY OF THE INVENTION

According to the present invention there is provided an electronic catheter displacement sensor comprising a displacement sensing roller and an idler roller between which a catheter can be advanced or retracted, means for sensing the rotation of the displacement sensing roller, means for determining the direction in which the displacement sensing roller is rotated, and means coupled to the rotation sensing means and to the direction sensing means for generating an output signal for transmission to a visual display device for displaying the distance the catheter has been advanced or retracted.

Further according to the present invention there is provided a sensor unit mounting the displacement sensing roller and the idler roller. The sensor unit includes a shaft mounted in the unit. The displacement sensing roller is mounted on the shaft. Coupling means are also mounted to the shaft for coupling the shaft to a rotatable element in the electronic catheter displacement sensor.

The coupling means is preferably realized by permanent magnets and the sensor unit is preferably a disposable unit.

BRIEF DESCRIPTION OF THE DRAWINGS

FIG. 7 is a vertical sectional view through the sensor unit shown in FIG. 6.

FIG. 8 is a bottom plan view with portions cut away of the sensor unit shown in FIG. 7 and with section lines omitted.

FIG. 9 is a vertical sectional view through the electronic displacement sensor shown in FIG. 6 and is taken along line 9—9 in FIG. 6.

DESCRIPTION OF THE PREFERRED EMBODIMENT(S)

Figure 1:
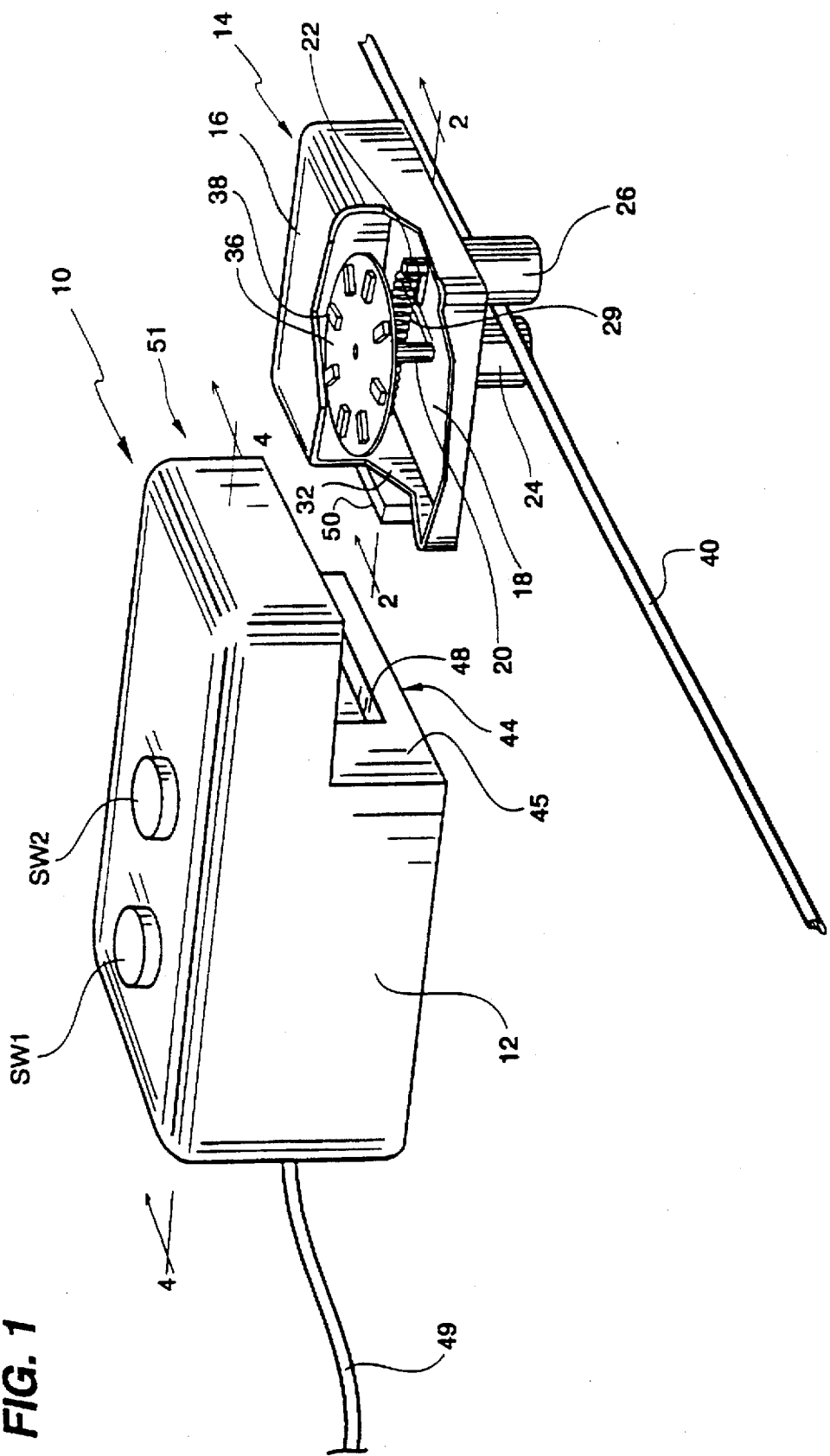
FIG. 1 is a perspective view of the electronic catheter displacement sensor of the present invention with a sensor unit thereof spaced outwardly from the displacement sensor.

Referring now to FIG. 1, there is illustrated therein an electronic catheter displacement sensor 10 constructed according to the teachings of the present invention. The sensor 10 includes a housing 12 and a sensor unit 14 which is shown separated from the housing 12.

The sensor unit 14 comprises a box 16 which is open on the lower end and has a plate 18 which is press-fitted into the box 16 and which has a sensing displacement roller shaft 20 and a idler roller shaft 22 mounted thereon.

Figure 3:
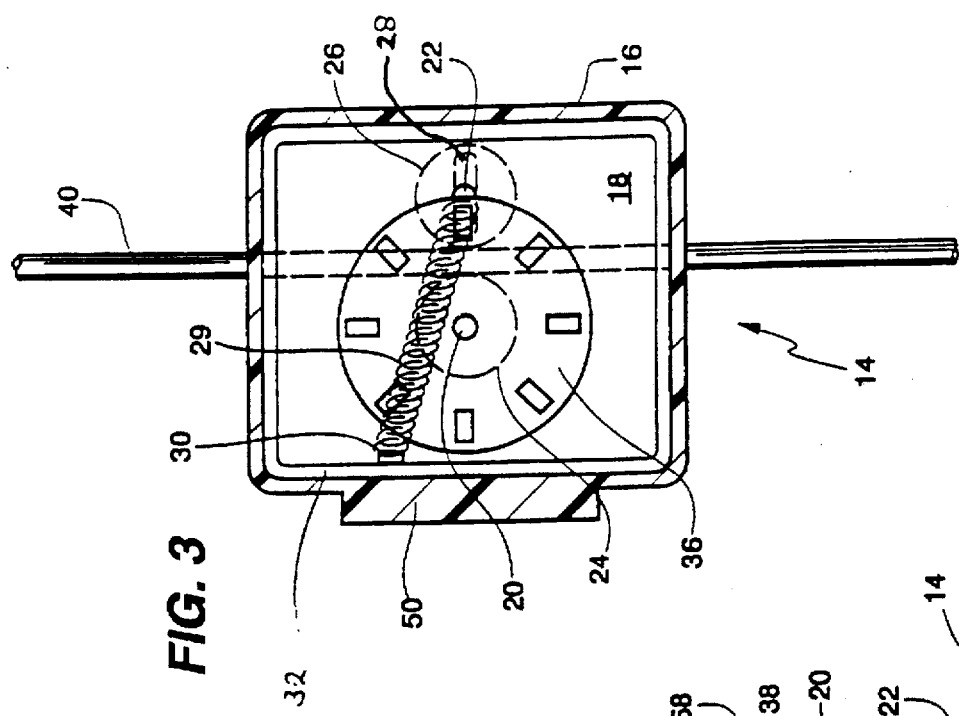
FIG. 3 is a generally horizontal sectional view of the sensor unit and is taken along line 3—3 of FIG. 2.
Figure 2:
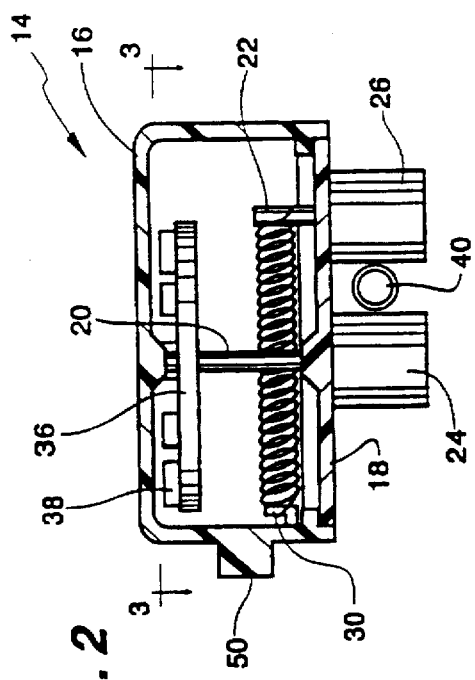
FIG. 2 is a vertical sectional view through the sensor unit shown in FIG. 1 and is taken along line 2—2 of FIG. 1.

As shown in FIG. 2, a displacement sensing roller 24 is mounted on the shaft 20 and an idler roller 26 is mounted on the shaft 22. The idler roller shaft 22 is received through a slot 28 (FIG. 3) in the plate 18. The upper end of the shaft 22 is connected to a spring 29 which extends across the box 16 to a hook 30 molded on an inside wall 32 of the box 16 for applying tension on the shaft 22 for the idler roller 26.

The displacement sensing roller 24 is mounted on the shaft 20 which extends into the box 16 and has mounted thereon a disk 36 having a plurality of (in the illustrated embodiment eight) permanent magnets 38 mounted equidistantly from each other around the periphery of the disk 36.

As shown in FIGS. 1–4, a catheter 40 is received between the displacement sensing roller 24 and the idler roller 26 and as the catheter 40 is advanced between the rollers 24, 26 or retracted between the rollers 24, 26, the disk 36 is rotated.

Figure 4:
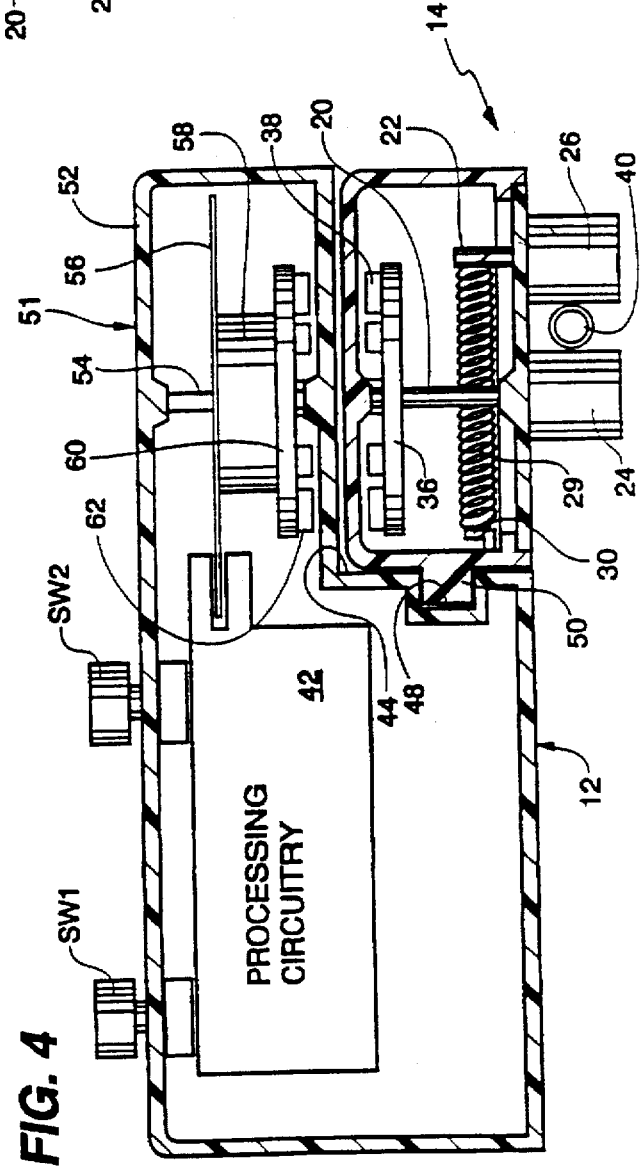
FIG. 4 is a generally vertical sectional view of the assembled electronic catheter displacement sensor and is taken along line 4—4 of FIG. 1.
Figure 5:
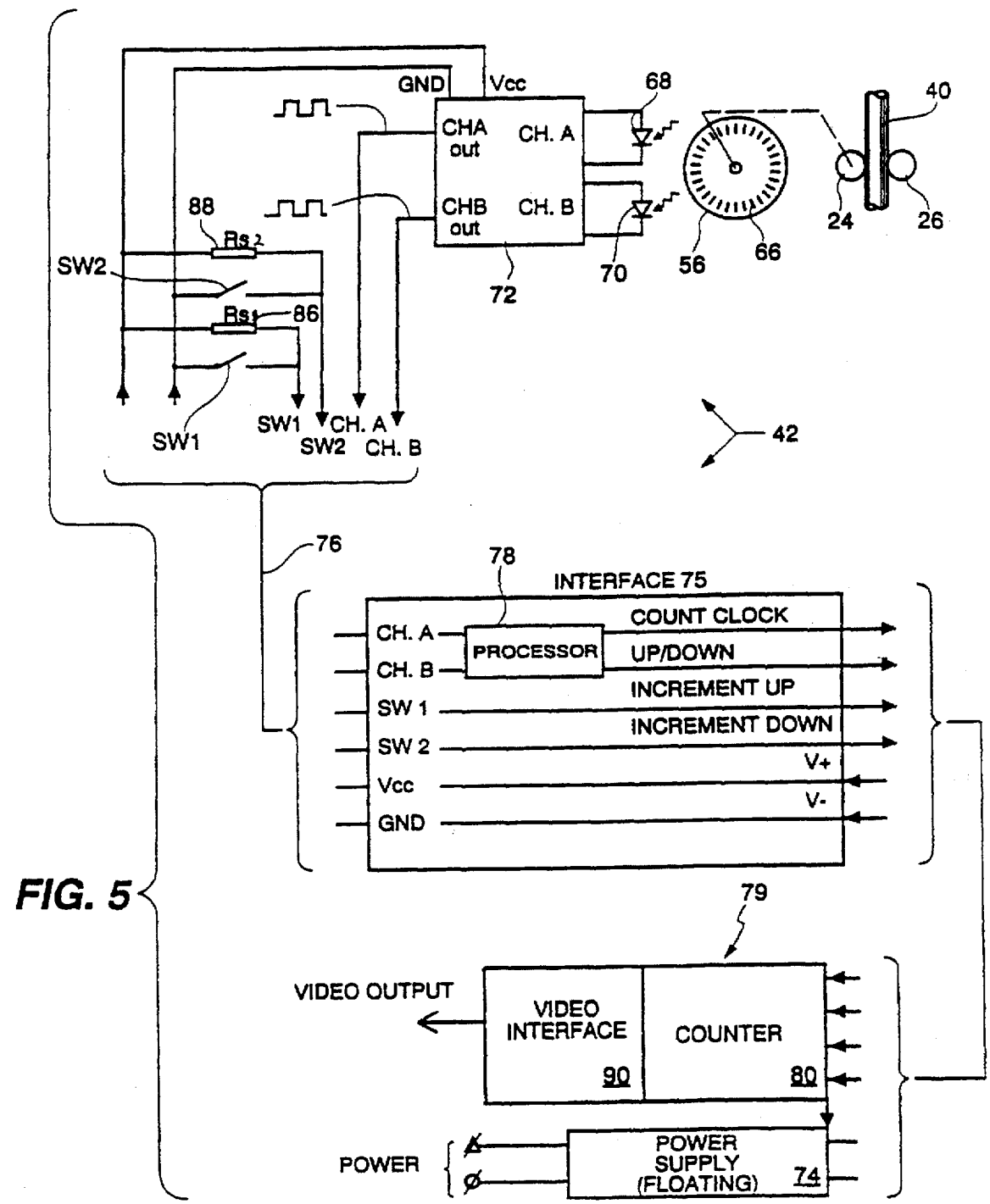
FIG. 5 is a schematic diagram, partly mechanical and partly electrical, of the electrical circuitry for converting the rotation of a catheter displacement sensing roller to an electrical signal directly related to the distance the catheter has been advanced and/or retracted and to the direction of advancement on retraction.

With reference to FIGS. 1, 4 and 5, the electronic catheter displacement sensor 10 comprises the housing 12 which has signal processing circuitry 42 therein and which has an open area 44 at a lower corner thereof for receiving the sensor unit 14. There is formed in a wall 45 defining part of the open area 44, a notch 48 for receiving a locating boss 50 molded on the outside of the wall 32 of the box 16 of the sensor unit 14. A power and data bus cable 49 extends from the housing 12.

As best shown in FIG. 4, located in an end portion 51 of the housing 12, above the open area 44 and extending downwardly from a top wall 52 of the housing is a shaft 54 that also extends through an upper code wheel 56 which is part of an optical incremental encoder to a rotor 58 having mounted on the lower end thereof a disk 60 substantially identical to the disk 36 in the sensor 14 and having a plurality of (in the illustrated embodiment eight) permanent magnets 62 mounted thereon. The two disks 36, 60 form a magnetic coupler for coupling the displacement sensing roller 24 to the code wheel 56.

It will be understood that rotation of the displacement sensing roller 24 will cause corresponding rotation of the rotor 58 mounting the code wheel 56.

As best shown in FIG. 5, the code wheel 56 has a plurality of equidistantly spaced slits or slots 66 therethrough and the code wheel 56 is positioned to rotate above two light sensitive diode pairs 68 and 70 of the processing circuitry 42. A light source, not shown, is positioned above the code wheel 56. A typical example of such an incremental encoder is the module H.E.D.S.-9100 manufactured by Hewlett Packard.

The code wheel 56 is not drawn to scale in FIG. 5 and preferably has 256 slots 66. Also, the displacement sensing roller 24 preferably has a circulation of 25.6 millimeters. In this way, with the displacement of 25.6 millimeters of the catheter 40, the code wheel 56 makes one revolution. This means that with a displacement of 0.1 millimeter, one pulse is delivered by the processing circuitry 42. In other words, the resolution is about 0.1 millimeter.

It will be noted that the housing 12 is totally enclosed and is not disposable but may be sterilized and reused.

The light source directs light at the top of the code wheel 56, and the light sensitive diode pairs 68 and 70 are positioned to receive light that passes through the slots 66.

A signal is generated in two channels—CH A and CH B which are shifted 90° in phase by amplifying and phase detection circuitry 72 mounted in the housing 42 and forming part of the processing circuitry 42.

A voltage supply 74 is provided for supplying +5 volts relative to ground to the phase shifting circuitry 72.

Because of the 90° phase shift of the light signals generated by light passing through the code wheel 56, the phase shift on Channels CH A and CH B from signals generated from the light sensitive diode pairs 68, 70, indicate whether the code wheel is being rotated clockwise or counter clockwise thereby to indicate whether the catheter 40 is being advanced or retracted.

The signals on Channels CH A and CH B are fed to an interface 75 via a six lead cable 76 which can have logical values.

In the interface 75, the Channel CH A and CH B signals, which are shifted 90° in phase, are translated by a processor 78 into a clock signal, e.g. a count clock and a direction signal, e.g. up or down.

In another processor unit 79 coupled to the interface 75, the signals are fed to a counter 80 which counts the clock pulses and senses the direction signal, that is to say the signals are counted up or counted down.

Two switches SW1 and SW2 are mounted on the housing 12 and are each connected through a resistor RS1, RS2 or a shunt circuit 86, 88, respectively, to the counter 80. By operating the switches SW1 or SW2, the counter 80 position can be adjusted up or down.

The processing unit 79 also contains a video interface 90 with which the counter position, which indicates how many steps the catheter has shifted in steps of 0.1 millimeter, is mixed with a standard video signal that also contains screen information, for instance, the information for an ultra-sound scanner or Roentgen equipment.

The power supply 74 is a floating power supply which supplies patient-safe power to the electronic displacement unit at the bedside of the patient. The visual display on the video screen of the video equipment and the size of the display can be programmed into the video receiver for display on a video screen, and the range of measurement value preferably will be from −999.9 millimeter to +999.9 millimeter.

In use, a catheter 40 is advanced manually by the physician between the displacement sensing roller 24 and the idler roller 26 into a vein or artery after the starting point has been preset with a switch SW3 (not shown), or preset with the switches SW1 or SW2. Then, the distance the catheter is advanced into a vessel is displayed on a television or video screen which can also display an image of the distal end of the catheter as it is being advanced through a blood vessel using an ultrasonic instrument.

In this way, when the catheter distal end reaches an area of interest, such as an area of stenosis, this can be visually seen on the television screen which is imaging the movement of the catheter in the blood vessel and at the same time the exact distance the catheter has been advanced into the blood vessel can be read off the visual display on the video screen.

In this respect, the distal end of the catheter can have an ultrasonic imaging device mounted therein which provides the image for the video screen. Then, after the ultrasonic imaging device at the distal end of the catheter is withdrawn by withdrawing the catheter, a balloon catheter can be inserted into the blood vessel and the distal end thereof advanced the exact distance in millimeters noted previously on the visual display on the video screen. In this way, exact placement of the balloon catheter is obtained.

The electronic catheter displacement system of the present invention provides several advantages. First of all, the disposable sensor unit 14 containing the magnet disk 36 and the rollers 24 and 26 ensures that there is no blood contamination, since each time the electronic displacement sensor is used with a new patient or a new procedure is carried out with the same patient and catheter displacement is to be sensed, a new disposable sensor unit 14 is used.

The cost for the sensor unit 14 is minimal, and sterility of the displacement sensor 10 is maintained at a minimal cost.

Another advantage is the provision of the processing circuity 42 within the housing 12 with the two adjustment switches SW1 and SW2 for "zeroing" the electronic displacement sensor. This housing unit can be used many times and provides (1) a magnetic coupling with the sensor unit 14 and (2) an electronic interface between the distance sensed by the electronic catheter displacement sensor unit 14 and a video screen whereby imaging of an area of interest in a body cavity or blood vessel and the distance a catheter has been advanced to that area of interest are shown simultaneously on the screen. This enables the distance to be recorded and then when another procedure, such as an angioplasty procedure, is carried out, the physician knows exactly how far to advance a balloon catheter into the blood vessel to place the distal end thereof in an area an interest, e.g., an area of stenosis.

Figure 6:
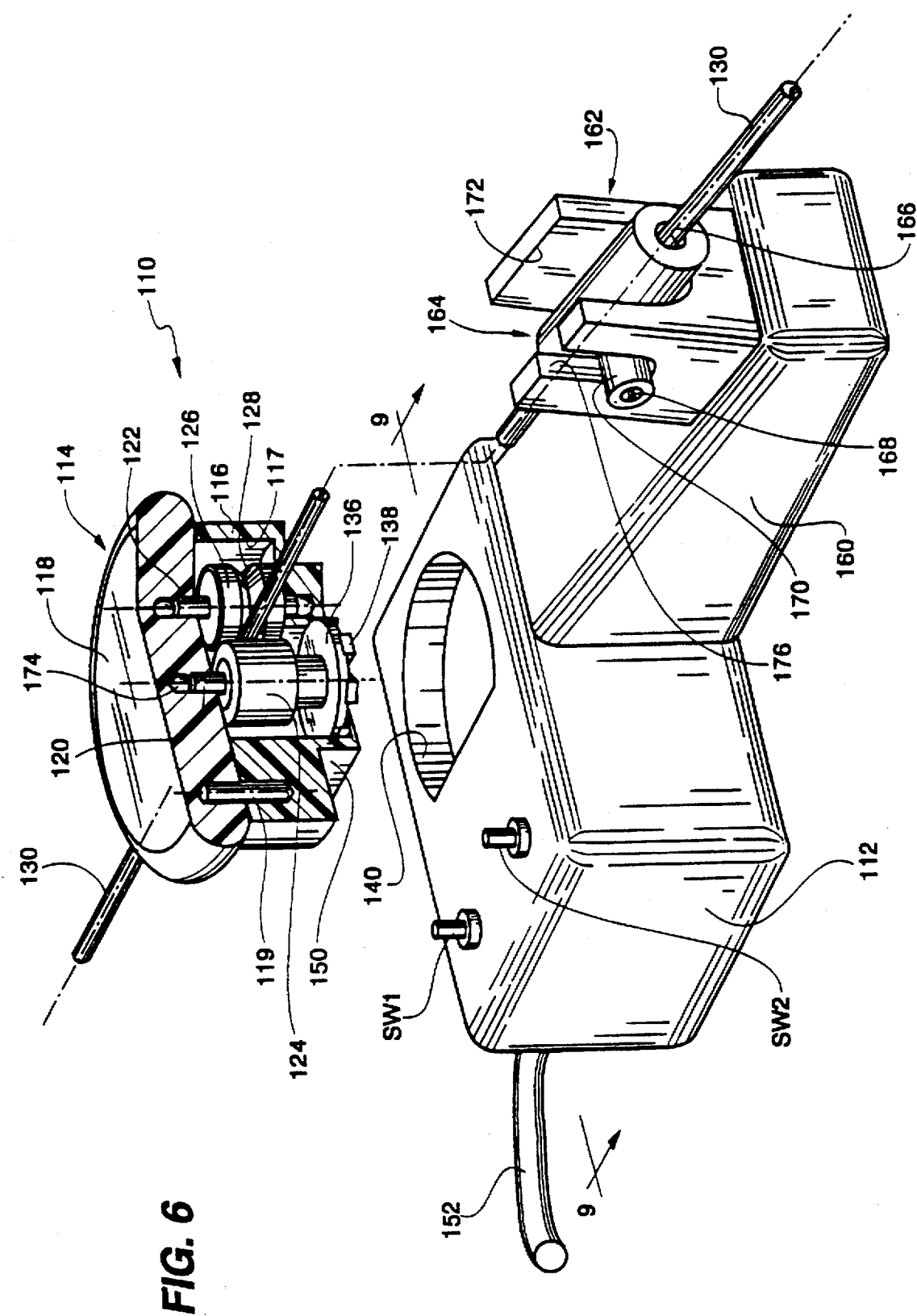
FIG. 6 is a perspective view of another embodiment of the electronic catheter displacement sensor with a sensor unit which is displaced upwardly from the remainder of the displacement sensor and which has portions cut away to show the rollers mounted therein.

Referring now to FIG. 6, there is illustrated therein another embodiment of an electronic catheter displacement sensor generally identified by the reference numeral 110.

Like the displacement sensor 10, the displacement sensor 110 includes a housing 112 and a sensor unit 114 which is shown in FIG. 6 separated from the housing 112. The sensor unit 114 comprises a body 116 having a hollow cavity 117 therein and an open top which is covered by a disk-shaped plate 118. The plate 118 has three holes therein which are aligned with three holes in the body 116 (FIG. 8). Each pair of aligned holes receive a pin 119 therein which fixes the plate 118 to the body 116. One pin 119 is shown in FIG. 6. The two other pins 119 are shown in FIG. 8 and extend between mating holes in the plate 118 and the body 116 for fixing the plate 118 to the body 116.

Extending downwardly from the plate from a hole in the plate to a mating hole in the portion of the body 116 opening onto the bottom of the cavity 117 is a sensing displacement roller shaft 120. Likewise, an idler roller shaft 122 extends between similar mating holes in the plate 118 and the body 116. A displacement sensing roller 124 is mounted on the shaft 120 and an idler roller 126 is mounted on the shaft 122. The idler roller 126 has an annular V-shaped groove 128 therein for receiving catheters of different sizes, and the sensing displacement roller 124 can be made of a yieldable elastomeric material, if desired, whereby catheters of different sizes can extend through the sensing unit 114.

Although not shown in detail, it will be understood that the body 116 has diametrically opposed entry and exit openings 131 and 132 therethrough, as shown in FIG. 8, through which the catheter 130 can extend. The entry opening 131 flares outwardly to facilitate insertion of a catheter into the sensor unit 114.

The catheter 130 extends through the aligned openings 131 and 132 in the body 116 and between the rollers 124 and 126, as shown in FIG. 9.

The shaft 120 mounting the displacement sensing roller 124 extends to the bottom of the cavity 117 in the body 116 and has mounted at the lower end thereof a disk 136 having a plurality of (in the illustrated embodiment eight) permanent magnets 138 mounted equidistantly from each other around the periphery of the disk 136.

As the catheter 130 is received between the displacement sensing roller 124 and the idler roller 126 and advanced therebetween, the disk 136 is rotated and a suitable mating disk (not shown in FIG. 6, but shown in FIG. 9 and identified by reference numeral 182) in the housing 112 is magnetically coupled to the disk 136 and is rotated a corresponding rotational distance, in a like manner, as the disks 36 and 60 shown in FIG. 4.

The housing 112 has a recess or cavity 140 therein which has the same configuration as a boss 150 at the lower end of the body 116 for receiving the boss 150 for supporting the sensing unit 114 on the top of the housing 112.

An electric power and data bus cable 152 extends from the housing 112 for connecting signal processing circuitry identical to the signal processing circuitry 42 shown in FIG. 5 to video equipment.

In a similar manner as in the embodiment shown in FIGS. 1–5, the housing 112 has two pushbutton switches SW 1 and SW 2 mounted on the top thereof.

The housing 112 further has a ramp shaped extension block 160 extending from one side thereof in line with the cavity 140 and has mounted thereon a U-shaped catheter guide block 162 in which is received a T-shaped tubular member 164 having a main throughbore 166 therethrough for receiving and guiding the catheter 130. The T-shaped tubular member 164 also has a side bore 168 in a side tubular portion 170. The U-shaped block 162 has a main U-shaped cavity 172 therein for receiving the T-shaped member 164 and a smaller transverse U-shaped recess 176 for receiving the side tubular portion 170 of the T-shaped member 164.

As best shown in FIG. 7, the idler roller shaft 122 can be supported between ball bearings received in the aligned holes in the body 116 and in the plate 118, as shown. Similarly, the upper end of the shaft 120 can engage a ball bearing 174 in the bottom of hole 175 in the plate 118.

As shown in FIG. 9, mounted inside the housing 112 is a rotor 180 mounted to a shaft (not shown) which extends from a top wall portion 181 of the housing 112 beneath the cavity 140. Mounted on the rotor 180 is a disk 182 having a plurality of (preferably eight) permanent magnets 184 mounted thereon for establishing a magnetic couple with the permanent magnets 138 on the disks 136 inside the sensor unit 114. At the bottom of the rotor 180 is a code wheel 186, similar to the code wheel 56 shown in FIG. 4. It will be understood that light is passed through the code wheel 186, which has slits therein, to a pair of light sensitive diode pairs (not shown) and the output signal from the diodes is supplied to electrical processing circuitry similar to the processing circuitry 42 shown in FIGS. 4 and 5.

Figure 10:
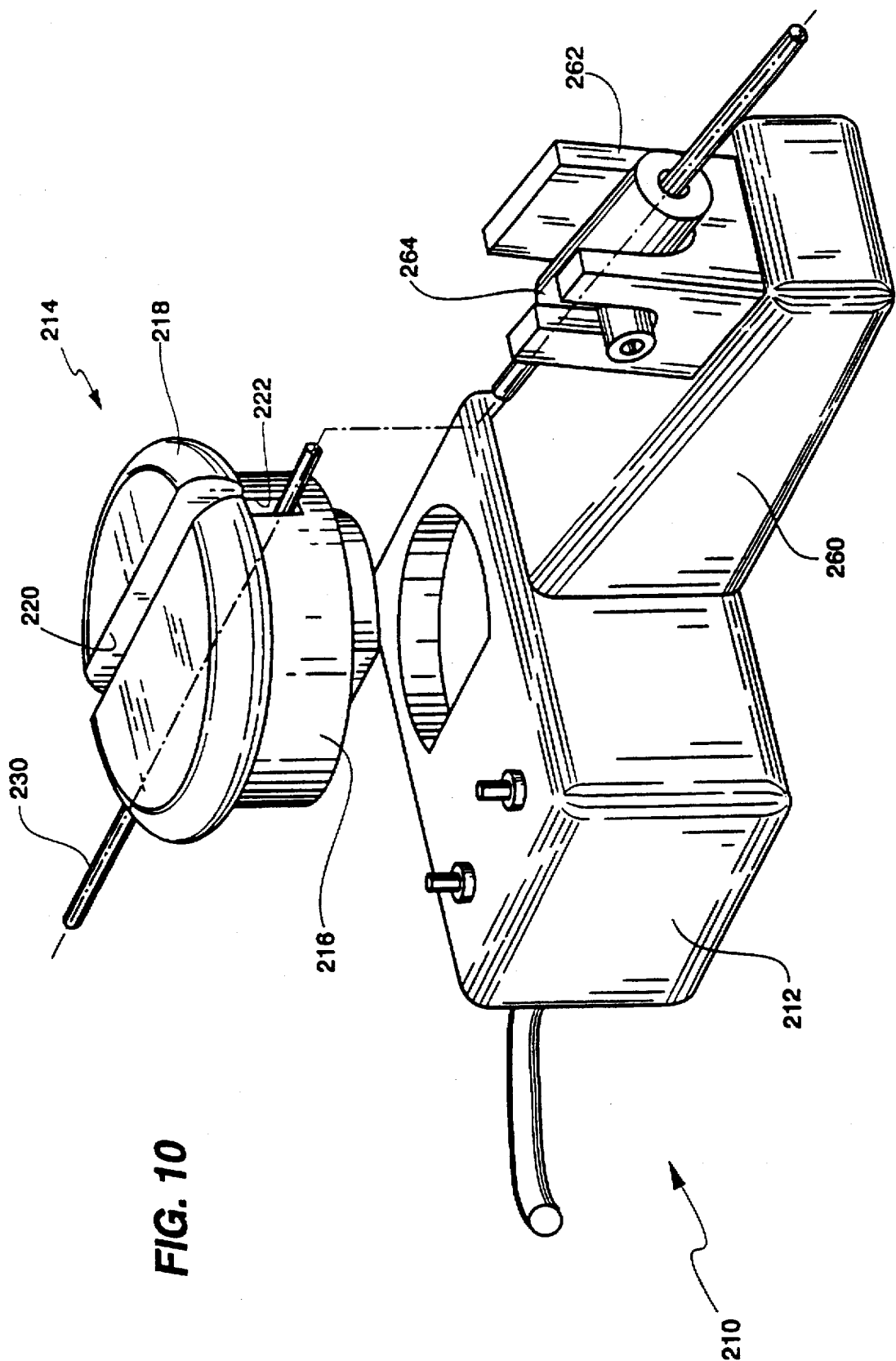
FIG. 10 is a perspective view of a modified embodiment of the electronic catheter displacement sensor shown in FIG. 6 with the sensor unit displaced upwardly, but not with portions cut away, and having a slot extending downwardly and across the sensor unit for receiving a catheter.

In FIG. 10 is shown a modified embodiment of another electronic catheter displacement sensor 220 having a housing 212 identical to the housing 112 and a sensing unit 214 which is similar to, but modified from, the sensor unit 114 shown in FIG. 6. Here, the sensor unit 214 comprises a body 216 and a top disk-shaped plate 218 having a slit 220 therethrough which communicates with a slit 222 in the body 216 whereby a catheter 230 can be inserted into the sensor unit from the top thereof, without having to be threaded through two openings and between a catheter displacement sensing roller and an idler roller, but merely placed between a displacement sensing roller and an idler roller (hidden from view in FIG. 10 and not show). In all other respects, the electronic catheter displacement sensor 210 is identical to the catheter displacement sensor 110 shown in FIG. 6 and includes a ramp shaped extension block 260, a U-shaped catheter guide block 262 and a T-shaped tubular member 264 identical to the parts numbered 160, 162 and 164 in the electronic catheter displacement sensor shown in FIG. 6.

From the foregoing description, it will be apparent that the electronic catheter displacement sensor 10 of the present invention has a number of advantages, some of which have been described above and others of which are inherent in the invention. Also, modifications can be made to the electronic catheter displacement sensor 10 without departing from the teachings of the invention. Accordingly, the scope of the invention is only to be limited as necessitated by the accompanying claims.

We claim:

1. An electronic catheter displacement sensor comprising a displacement sensing roller and an idler roller between which a catheter can be advanced or retracted, means for sensing the rotation of the displacement sensing roller, means for determining the direction in which the displacement sensing roller is rotated, means coupled to said rotation sensing and direction sensing means for generating an output signal for transmission to a visual display device for displaying the distance the catheter has been advanced or retracted, a disposable sensor unit mounting said displacement sensing roller and said idler roller, a shaft mounted in said sensor unit, said displacement sensing roller being mounted on said shaft and coupling means mounted to said shaft for coupling said shaft to a rotatable element in said electronic catheter displacement sensor, said sensor unit comprising a sealed box, said coupling means comprising a disk having a plurality of magnets spaced equidistantly adjacent the periphery of the disk mounted on said shaft within said box, with said displacement sensing roller being mounted on said shaft and a stub shaft rotorably journaled in a wall of said box for mounting said idler roller in said box, a housing for said catheter displacement sensor, said means for sensing rotation of said displacement sensing roller and for sensing the direction of rotation of said displacement sensing roller comprising an optical incremental encoder, and said means for generating an output signal comprising processing circuitry including an up/down counter mounted in said housing.

2. The electronic catheter displacement sensor of claim 1 wherein said incremental encoder provides a first output channel and a second output channel, said channels being phase shifted 90° from each other whereby the direction of rotation can be determined, up or down, and wherein said processing circuitry includes a processor, said signals from said first and second channels being supplied to said processor which outputs a count clock signal and an up/down signal, said processing circuitry further including a processing unit coupled to the output of said processor for receiving said count clock signal and said up/down signal, said processing circuitry including a counter having its output coupled to a video interface providing a video output.

3. An electronic catheter displacement sensor comprising a displacement sensing roller and an idler roller between which a catheter can be advanced or retracted, a housing for said displacement sensor, means for sensing the rotation of the displacement sensing roller, means for determining the direction in which the displacement sensing roller is rotated, and means coupled to said rotation sensing and direction sensing means for generating an output signal for transmission to a visual display device for displaying the distance the catheter has been advanced or retracted, said means for sensing rotation of said displacement sensing roller and for sensing the direction of rotation of said displacement sensing roller comprising an optical incremental encoder, said means for generating an output signal comprising processing circuitry including an up/down counter, and a video interface connected to the output of said processing circuitry and a floating power supply mounted in said housing for supplying operating voltage and current to said processing circuitry.

4. An electronic catheter displacement sensor comprising a displacement sensing roller and an idler roller between which a catheter can be advanced or retracted, a housing for said displacement sensor, means for sensing the rotation of the displacement sensing roller, means for determining the direction in which the displacement sensing roller is rotated, and means coupled to said rotation sensing and to said direction sensing means for generating an output signal for transmission to a visual display device for displaying the distance the catheter has been advanced or retracted, said means for sensing rotation of said displacement sensing roller and said means for sensing the direction of rotation of said displacement sensing roller comprising an optical incremental encoder, said means for generating an output signal comprising processing circuitry including an up/down counter, said incremental encoder provides a first output channel and a second output channel, said channels being phase shifted 90° from each other whereby the direction of rotation can be determined, up or down, said processing circuitry including a processor, said signals from said first and second channels being supplied to said processor which outputs a count clock signal and an up/down signal, said processing circuitry further including a processing unit coupled to the output of said processor for receiving said count clock signal and said up/down signal, said processing circuitry including a counter having its output coupled to a video interface providing a video output, a first switch and a second switch, said switches being mounted either to said housing or mounted to said processing unit, each switch being coupled across a resistor, for supplying an increment up signal upon actuation of the first switch and an increment down signal upon actuation of the second switch, the output of said switches being coupled to the input of said processing unit for being supplied to said counter of said processing unit.

5. An electronic catheter displacement sensor comprising a displacement sensing roller and an idler roller between which a catheter can be advanced or retracted, a housing for said displacement, means for sensing the rotation of the displacement sensing roller, means for determining the direction in which the displacement sensing roller is rotated, and means coupled to said rotation sensing means and to said direction sensing means for generating an output signal for transmission to a visual display device for displaying the distance the catheter has been advanced or retracted, said means for sensing rotation of said displacement sensing roller and said means for sensing the direction of rotation of said displacement sensing roller comprising an optical incremental encoder, said means for generating an output signal comprising processing circuitry including an up/down counter, and guide means mounted to said housing for receiving and guiding a catheter from said electronic displacement sensor.

6. A sensor unit comprising a displacement sensing roller, an idler roller, a shaft mounted in said sensor unit said displacement sensing roller being mounted on said shaft, and means mounted to said shaft for coupling said shaft to a rotatable element in an electronic catheter displacement sensor.

7. An electronic catheter displacement sensor, comprising:

a housing for said displacement sensor;

a disposable sensor unit;

said disposable sensor unit comprising a sealed box, a sensing roller and an idler roller between which a catheter can be advanced and retracted;

said housing having mounted therein, a rotatable element, means for sensing the rotation of said rotatable element and means for determining the direction in which said rotatable element is rotated, and means coupled to said rotation sensing and direction sensing means for generating an output signal corresponding to the distance and direction of rotation of said rotatable element;

said electronic catheter displacement sensor further comprising magnetic coupling means for coupling said sensing roller and said rotatable element, said magnetic coupling means comprising a first magnetic means arranged for rotation in said sealed box, said first magnetic means being driven for rotation by the rotation of said sensing roller, said magnetic coupling means comprising a second magnetic means arranged for rotation in said housing, and said second magnetic means driving said rotatable element for rotation.

* * * * *

UNITED STATES PATENT AND TRADEMARK OFFICE
CERTIFICATE OF CORRECTION

PATENT NO. : 5,709,661
DATED : January 20, 1998
INVENTOR(S) : Franciscus Cornelis Van Egmond and Charles Theodoor Lancee It is certified that error appears in the above-indentified patent and that said Letters Patent is hereby corrected as shown below:

Column 7, line 41, "show" should be --shown--.

Column 8, line 11, "rotorably" should be --rotatably--.

Signed and Sealed this

Sixth Day of July, 1999

*Attest:*

Q. TODD DICKINSON

*Attesting Officer*    Acting Commissioner of Patents and Trademarks

UNITED STATES PATENT AND TRADEMARK OFFICE
CERTIFICATE OF CORRECTION

PATENT NO. : 5,709,661
DATED : January 20, 1998
INVENTOR(S) : Franciscus Cornelis Van Egmond and Charles Theodoor Lancee It is certified that error appears in the above-identified patent and that said Letters Patent is hereby corrected as shown below:

On the title page: Item [73]

Assignee: Please change the name of the city "Eijswijk" to --Rijswijk--; and please change the name of the assignee "Endo Sonics Europe B.V." to --EndoSonics--.

Signed and Sealed this

Twelfth Day of October, 1999

Attest:

Q. TODD DICKINSON

*Attesting Officer*  *Acting Commissioner of Patents and Trademarks*